(12) United States Patent
Abu Bakar

(10) Patent No.: US 9,192,640 B2
(45) Date of Patent: Nov. 24, 2015

(54) ANTIVIRAL COMPOSITION AGAINST FLAVIVIRUS

(71) Applicant: University Malaya, Kuala Lumpur (MY)

(72) Inventor: Sazaly Abu Bakar, Kuala Lumpur (MY)

(73) Assignee: Universiti Malaya, Kuala Lumpur (MY)

( * ) Notice: Subject to any disclaimer, the term of this patent is extended or adjusted under 35 U.S.C. 154(b) by 0 days.

(21) Appl. No.: 14/384,378

(22) PCT Filed: Jan. 16, 2013

(86) PCT No.: PCT/MY2013/000008
§ 371 (c)(1),
(2) Date: Sep. 10, 2014

(87) PCT Pub. No.: WO2013/147584
PCT Pub. Date: Oct. 3, 2013

(65) Prior Publication Data
US 2015/0038571 A1 Feb. 5, 2015

(30) Foreign Application Priority Data
Mar. 30, 2012 (MY) .............................. PI2012700142

(51) Int. Cl.
*A61K 31/352* (2006.01)
*A61K 36/539* (2006.01)

(52) U.S. Cl.
CPC ............. *A61K 36/539* (2013.01); *A61K 31/352* (2013.01)

(58) Field of Classification Search
CPC .......................... A61K 31/352; A61K 36/539
See application file for complete search history.

(56) References Cited

U.S. PATENT DOCUMENTS

2008/0161324 A1  7/2008  Johansen et al.
2010/0086627 A1  4/2010  Zabrecky

OTHER PUBLICATIONS

Sanchez et al. (Phytother. Res. 14, 89-92 (2000)).*
Zandi et al. (Virology Journal 2011, 8:560).*
"International Search Report received in PCT/MY2013/000008, mailed May 15, 2013".

* cited by examiner

*Primary Examiner* — Valerie Rodriguez-Garcia
(74) *Attorney, Agent, or Firm* — Suzannah K. Sundby, Esq.; Canady + Lortz LLP

(57) ABSTRACT

The present invention relates to a composition having antiviral activity for prophylaxis or treatment of flavivirus infection or a disease resulting therefrom in humans or animals, characterized in that said composition consisting of baicalein, or analogs, or derivatives thereof. The composition may further comprise a pharmaceutically acceptable carrier. The antiviral activity may include inhibition of virus attachment to host cells, inhibition of intracellular virus replication and direct virucidal activity. The flavivirus may comprise dengue virus type-1, dengue virus type-2, dengue virus type-3, dengue virus type-4 and Japanese encephalitis virus.

Figure 1:
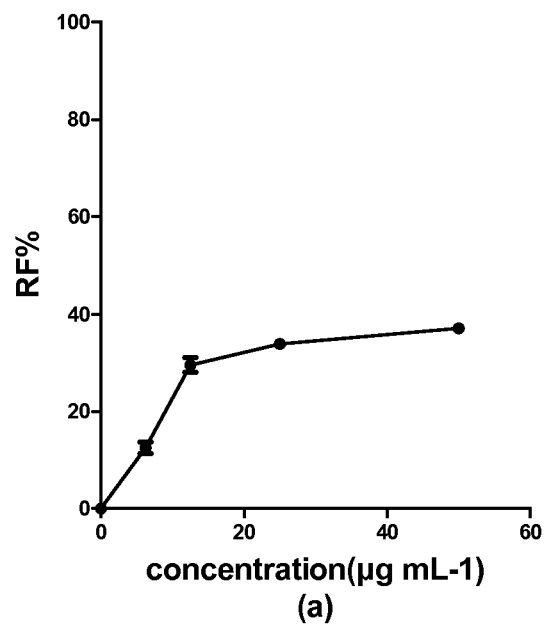
Figure 1:
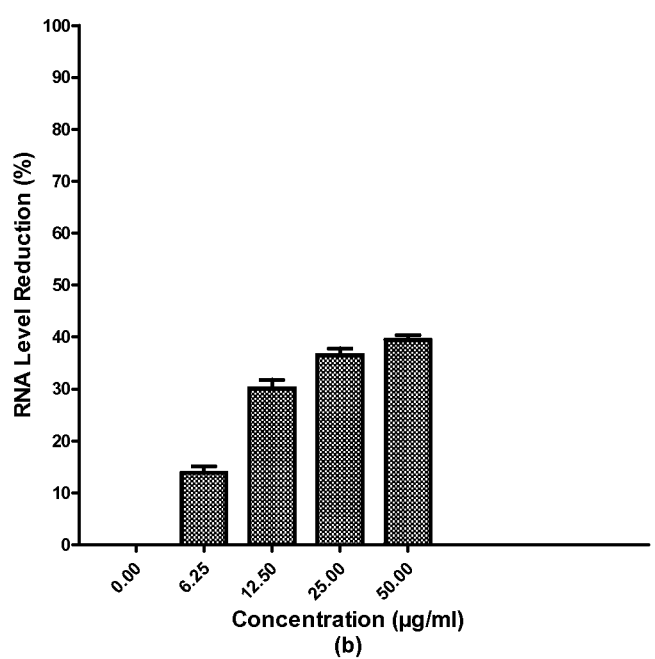

10 Claims, 6 Drawing Sheets

ANTIVIRAL COMPOSITION AGAINST FLAVIVIRUS

BACKGROUND OF THE INVENTION

1. Field of the Invention

This invention relates to a composition having antiviral activity for prophylaxis or treatment of positive-stranded RNA virus infection or a disease, and more particularly to the composition comprising flavonoid baicalein for prophylaxis or treatment of a flavivirus infection.

2. Description of Related Arts

The positive-stranded RNA virus including flavivirus family comprises many medically important viruses which include dengue, a serious mosquito-borne disease common in the tropics and sub-tropical regions of the world. Dengue has caused many deaths and afflicted millions of people annually and threatened almost 2.5 billion people living in the regions. It is amongst the most rapidly spreading mosquito-borne viral infection.

Dengue is caused by dengue virus a member of the genus flavivirus, family Flaviviridae, a positive-strand RNA virus. Other common medically important virus in this family includes Japanese encephalitis virus, Yellow fever virus, Hepatitis C virus, West Nile encephalitis virus, Murray Valley encephalitis virus, Tick-borne encephalitis virus, St. Louis encephalitis virus and Kyasanur Forest disease virus. Infection by any of these viruses results in a wide spectrum of clinical illnesses ranging from a silent asymptomatic or mild febrile infection, self-limited infection to the severe encephalitis, hepatitis and deaths. Similarly, dengue can manifests as self-limited dengue fever (DF) to severe dengue hemorrhagic fever (DHF) and dengue shock syndrome (DSS). There are four serotypes or genotypes of dengue virus, dengue virus type-1 (DENV-1), dengue virus type-2 (DENV-2), dengue virus type-3 (DENV-3) and dengue virus type-4 (DENV-4) which are transmitted to human by at least two species of mosquitoes, Aedes agypti and Aedes albopictus. All four dengue virus genotypes cause similar clinical symptoms. The mechanisms of how one contracted severe dengue is still unknown. The severity of dengue is said to be directly correlated to the amount of virus present in a person's blood.

To date, there is no approved therapeutics or antiviral therapy for the treatment of most of the flavivirus infection if not all of them, including dengue. There is no effective antiviral that can help to reduce dengue virus load in patients to prevent the severe manifestation of dengue, DHF or DSS. Due to the rapidly expanding dengue disease globally, it is critical to develop an effective antiviral drugs or acceptable vaccines against dengue. Effort to prevent dengue using vaccine is plagued with many potential issues and risks. Therefore, an effective drug that can help to reduce dengue virus load during early stage of infection is much desired.

Plants and plant derived compounds remained an important source of new antiviral drugs due to their potential low side effects and their ubiquitous accessibility in nature. There have been a few reports on antiviral activities of various phytochemicals against dengue viruses. Among these include the flavonoids. Flavonoids are low molecular weight phenolic compounds found widely in different types of plants. Different types of flavonoids can be found in fruits, roots, nuts, seeds, bark, steams and flowers of plants. Baicalein (5,6,7-Trihydroxyflavone), which is a type of flavonoid, is found in the roots of a number of herbal plants.

Antiviral activities of baicalein have been evaluated against a number of common human viruses which include the double-stranded DNA viruses, herpesviruses and few negative-stranded respiratory viruses but none that demonstrate it as inhibitor of a positive-stranded RNA virus replication. The application of baicalein as an effective inhibitor of the positive-stranded RNA virus, more specifically the flavivirus, dengue virus replication is emphasized in the present invention.

US Patent Application Publication No. 2010/0004325 A1 disclosed a new molecular and cellular effect of baicalein, which is selected by a proxlylhydroxylase 2 (PHD2) inhibitor screening method using a compound library. The cited art analysed the hypoxia inducible factor (HIF) protein expression induced by baicalein in cells, quantitatively analyzed the inhibitory effect of baicalein against PHD2, confirmed the inhibitory effect against factor inhibiting HIF, and confirmed whether VEGF is expressed by using a reporter assay and ELISA. The cited art proved that baicalein can be used as a drug to treat ischemic disease, and other related diseases. Nonetheless, the cited art did not mention specific composition of baicalein that will work as inhibitor against flavivirus replication. Therefore, there is a need to have a certain workable composition or concentration of baicalein that exhibit antiviral property, particularly to dengue virus. Besides that, there is a need to maximise the potential of baicalein for reducing viral RNA replication in treating and preventing infectious diseases triggered by RNA viruses belonging to the genus of Flavivirus by having different concentrations of baicalein to exhibit direct virucidal activity, prophylactic property, and anti-attachment activity.

US Patent Application Publication No. 2008/0176932 A1 is an invention that relates to a pharmaceutical composition having synergistic anti-tumour effects, more specifically to a pharmaceutical composition comprising of flavonoids. The cited art further relates to the preparation and pharmaceutical use of the composition, which contains baicalein and baicalin or scutellarin. The cited prior art also disclosed compositions of baicalein and baicalin or scutellarin and its related compound that exhibit anti-tumour effects, but did not mention the composition on flavivirus replication. Therefore, there is a need to have a composition or a compound that exhibit antiviral property and inhibit flavivirus replication, particularly in dengue virus and Japanese encephalitis virus.

U.S. Pat. No. 6,083,921 relates to pharmaceutical compositions having antiviral, antibacterial, or immune modulating property in general and in particular to pharmaceutical compositions useful in the treatment or prevention of infection by parainfluenza or respiratory syncytial virus. The pharmaceutical compositions are obtained from combinations of plants containing baicalin, chlorogenic acid, and forsythiaside particularly in isolated and purified form. The pharmaceutical composition usefulness does not extend to positive stranded RNA viruses particularly flavivirus. Therefore, there is a need to resolve the cited prior art by having a composition consisting of baicalein as the active antiviral ingredient, to treat and prevent infection caused by the positive-stranded RNA virus such as the flavivirus, for example dengue virus and Japanese encephalitis virus.

SUMMARY OF INVENTION

It is an objective of the present invention to provide a composition having antiviral activity for prophylaxis or treatment of flavivirus infection or a disease resulting therefrom.

It is an objective of the present invention to provide the composition having antiviral activity for prophylaxis or the treatment of dengue virus infection or Japanese encephalitis virus infection.

It is also an objective of the present invention to provide the composition having antiviral activity comprises inhibition of virus replication, reduction in virus yield, virucidal activity and inhibition of virus attachment to host cells.

Figure 6:
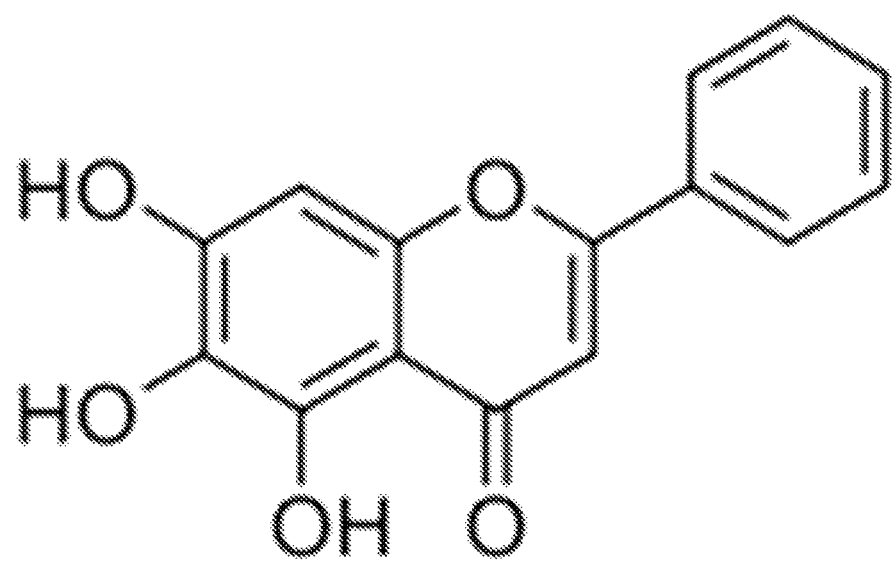

Accordingly, these objectives may be achieved by following and extending the demonstration of the present invention. The present invention relates to a composition having antiviral activity for prophylaxis or treatment of flavivirus infection or a disease resulting therefrom in humans or animals, characterised in that said composition consisting of baicalein, or analogues, or derivatives thereof

BRIEF DESCRIPTION OF THE DRAWINGS

The features of the invention will be more readily understood and appreciated from the following detailed description when read in conjunction with the accompanying drawings of the preferred embodiment of the present invention, in which:

FIG. 1(*a*) is a graph showing reduction in the percentage of dengue virus foci (RF %) after treating dengue virus infected Vero cells with different concentrations of baicalein when added before infection with dengue virus.

FIG. 1(*b*) is a graph showing reduction in the level of dengue virus RNA after treating dengue virus infected Vero cells with different concentrations of baicalein added before infection with dengue virus.

FIG. 2(*a*) is a graph showing reduction in the percentage of dengue virus foci (RF %) after treating dengue virus infected Vero cells with different concentrations of baicalein, added simultaneously during infection with dengue virus.

FIG. 2(*b*) is a graph showing reduction in the level of dengue virus RNA after treating dengue virus infected Vero cells with different concentrations of baicalein added simultaneously during infection with dengue virus.

FIG. 3(*a*) is a graph showing reduction in the percentage of dengue virus foci (RF %) after treating dengue virus infected Vero cells with different concentrations of baicalein, added after infection with dengue virus.

FIG. 3(*b*) is a graph showing reduction in the level of dengue virus RNA after treating dengue virus infected Vero cells with different concentrations of baicalein added after infection with dengue virus.

FIG. 4(*a*) is a graph showing reduction in the percentage of dengue virus foci (RF %) after directly treating dengue virus with different concentrations of baicalein.

FIG. 4(*b*) is a graph showing reduction in the level of dengue virus RNA after directly treating dengue virus with different concentrations of baicalein.

FIG. 5 is a graph showing reduction in the percentage of Japanese Encephalitis Virus (JEV) foci (RF %) after treating JEV infected Vero cells with different concentrations of baicalein, added after infection with JEV.

FIG. 6 is a molecular structure of baicalein.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting but merely as a basis for claims. It should be understood that the drawings and detailed description thereto are not intended to limit the invention to the particular form disclosed, but on the contrary, the invention is to cover all form of modifications, equivalents and alternatives falling within the scope of the present invention as defined by the appended claims. As used throughout this application, the word "may" is used in a permissive sense (i.e., meaning having the potential to), rather than the mandatory sense (i.e., meaning must). Similarly, the words "include," "including," and "includes" mean including, but not limited to. Further, the words "a" or "an" mean "at least one" and the word "plurality" means one or more, unless otherwise mentioned. Where the abbreviations of technical terms are used, these indicate the commonly accepted meanings as known in the technical field. For ease of reference, common reference numerals will be used throughout the figures when referring to the same or similar features common to the figures. The present invention will now be described with reference to FIG. 1-5.

The present invention relates to a composition having antiviral activity for prophylaxis or treatment of flavivirus infection or a disease resulting therefrom in humans or animals, characterised in that said composition comprises baicalein, or analogues, or derivatives thereof. The terms "analogues or derivatives" as used herein also includes salts, solvates, hydrates, prodrugs, and isomers including tautomers and stereoisomers of baicalein.

In a preferred embodiment of the present invention, said baicalein is in a concentration range of about 0.1 to 100% by weight.

In a preferred embodiment of the present invention, the effective concentrations of said composition are in a range of 1.6 μg/ml (1.56 μg/ml) to 100.0 μg/ml.

In a preferred embodiment of the present invention, said baicalein is extracted from roots of plant *Scutellaria baicalensis*.

In a preferred embodiment of the present invention, said composition is formulated with a pharmaceutically acceptable carrier.

In a preferred embodiment of the present invention, the effective concentration of said composition having antiviral activity comprises 50 μg/ml-100 μg/ml of baicalein.

In a preferred embodiment of the present invention, the antiviral activity is virucidal activity.

In a preferred embodiment of the present invention, the effective concentration of said composition having virucidal activity comprises 12.5 μg/ml of baicalein.

In a preferred embodiment of the present invention, the effective concentration of said composition is used in prophylaxis of Flavivirus infection or a disease resulting therefrom in humans or animals comprises 50 μg/ml of baicalein.

In a preferred embodiment of the present invention, the antiviral activity is inhibition of virus attachment to host cells.

In a preferred embodiment of the present invention, the effective concentration of said composition having inhibition of virus attachment to host cells comprises 25 μg/ml of baicalein.

In a preferred embodiment of the present invention, the flavivirus is selected from a group comprising dengue virus type-1, dengue virus type-2, dengue virus type-3, dengue virus type-4, and Japanese encephalitis virus.

In a preferred embodiment of the present invention, said composition is for prophylaxis or treatment of dengue virus type-2 and Japanese encephalitis virus.

A person skilled in the art may attempt to modify the molecular structure of baicalein for the purpose similar to present invention. It is possible for such modification by adding, removing, or substituting moieties in the baicalein compound. Said baicalein may be modified by means of esterification, hydrolysis, saponification, resulting in substitution in one or more positions or any other chemical processes.

FIG. 6 shows the molecular structure of baicalein.
Compound Baicalein

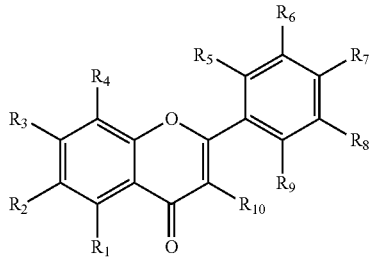

Formula 1

In a preferred embodiment, baicalein according to formula 1, or an analogue or derivative thereof, according to formula 1, including salts, solvates, hydrates, prodrugs, and isomers including tautomers or stereoisomers of baicalein, wherein:

$R_1$, $R_2$, $R_3$, $R_4$, $R_5$, $R_6$, $R_7$, $R_8$, $R_9$, and $R_{10}$, which are each independently selected from the group consisting of: —H, —OH, —OR', —SH, —SR', —SOR', —NO$_2$, —NH$_2$, —NHR', —N(R')$_2$, —NHCOR', —N(COR')$_2$, —NHSO$_2$R', —CN, halogen, —C(═O)H, —C(═O)R', —CO$_2$H, —CO$_2$R', alkyl, substituted alkyl, alkenyl, substituted alkenyl, cycloalkenyl, substituted cycloalkenyl, alkynyl, substituted alkynyl, aryl, substituted aryl, heterocyclyl, substituted heterocyclyl, heteroaryl and substituted heteroaryl;

wherein each substituted alkyl, substituted cycloalkyl, substituted alkenyl, substituted cycloalkenyl, substituted alkynyl, substituted aryl, substituted heteroaryl, and/or substituted heterocyclyl has 1-3 substituents each independently selected from the group consisting of:

—OH, —OR', —SH, —SR', —SOR', —SO$_2$R', —NO$_2$, —NH$_2$, —NHR', —N(R')$_2$, —NHCOR', —N(COR')$_2$, —NHSO$_2$R', —CN, halogen, —C(═O)H, —C(═O)R', —CO$_2$H, —CO$_2$R', alkyl, alkyl substituted with 1-3 R'', alkenyl, alkenyl substituted with 1-3 R'', cycloalkenyl, cycloalkenyl substituted with 1-3 R'', alkynyl, alkynyl substituted with 1-3 R'', aryl, aryl substituted with 1-3 R'', heterocyclyl, heterocyclyl substituted with 1-3 R'', heteroaryl and heteroaryl substituted with 1-3 R'';

wherein each R' is independently selected from the group consisting of alkyl, alkyl substituted with 1-3 R'', cycloalkyl, cycloalkyl substituted with 1-3 R'', alkenyl, alkenyl substituted with 1-3 R'', cycloalkenyl, cycloalkenyl substituted with 1-3 R'', alkynyl, alkynyl substituted with 1-3 R'', aryl, aryl substituted with 1-3 R'', alkylaryl, alkylaryl substituted with 1-3 R'', heterocyclyl, heterocyclyl substituted with 1-3 R'', heteroaryl and heteroaryl substituted with 1-3 R''; and wherein each R'' is independently selected from the group consisting of: —OH, —SH, —NO$_2$, —NH$_2$, —CN, halogen, —C(═O)H, and —CO$_2$H.

In a preferred embodiment, the alkyl is methyl, ethyl, n-propyl, iso-propyl, n-butyl, iso-butyl, sec-butyl, tert-butyl, n-pentyl, 1-methylbutyl, 2-methylbutyl, 3-methylbutyl or 2,2'-dimethylpropyl. In a preferred embodiment, the aryl comprises 4-10 carbon atoms. In a preferred embodiment, the cycloalkyl comprises 3-6 carbon atoms.

In a preferred embodiment, the $R_1$, $R_2$, and $R_3$ are —OH.
In a preferred embodiment, the $R_4$, $R_5$, $R_6$, $R_7$, $R_8$, $R_9$, and $R_{10}$ are —H.
Baicalein has a molecular formula of $C_{15}H_{10}O_5$.

While it may be possible for the baicalein to be administered alone, it is preferable to present them with the pharmaceutically acceptable carrier. Said carrier(s) optimally are acceptable in the sense of being compatible with other ingredients or compounds of said composition and not deleterious for any administration routes including oral, rectal, nasal, topical, vaginal, or parenteral administration.

In a preferred embodiment, the pharmaceutically acceptable carrier comprises water, solvents, pH buffering agents, stabilisers, excipients, diluents, or mixtures thereof. As used herein, the term "pharmaceutically acceptable carrier" means inert, non-toxic solid or liquid filler, diluent or encapsulating material, not reacting with the active ingredients according to the present invention, which is baicalein. These carriers are known to the man versed in the art. Wetting agents and emulsifiers, as well as release agents, coating agents, and preservatives may also be present in the preparations of the present invention. The amount of baicalein that may be combined with the carrier materials to produce a single dosage form will vary, depending upon the patient treated and the particular mode of administration.

The term "pharmaceutically acceptable carrier" herein also includes food additives generally used in foods and drinks, such as a sweetener, a colouring agent, a preservative, a thickening stabiliser, an antioxidant, a colour developing agent, a bleaching agent, a bitter agent, an enzyme, a sour agent, a seasoning, a nutrient supplement, a manufacture facilitating agent, and a flavour.

The composition of the present invention formulated with a pharmaceutically acceptable carrier may be prepared in any appropriate manner, for instance by homogenously mixing, coating and/or grinding baicalein, in a one-step or multi-step procedure.

Said composition may conveniently be presented in unit dosage form and may be prepared by any method in the art of pharmacy. Such methods may include homogenising said composition with a chosen carrier before shaping product of the homogenisation into a unit dosage form such as cream.

In a preferred embodiment of the present invention, said composition can be formulated for any suitable route of administration, depending on whether local or systemic treatment is desired and which area is to be treated. Said composition may be prepared and formulated for parenteral administration, such as intravenous, intraperitoneal, intramuscular, or subcutaneous injection. Said composition of the present invention may also be prepared and formulated in a conventional form either as liquid solution or emulsion, or solid form for solubilising in liquid, which is suitable for injection. Said parental administration may involve preparation including the use of sterile aqueous or non-aqueous solutions, and emulsions. Some examples of non-aqueous solvents that could be used in formulating said composition of the present invention are propylene glycol polyethylene glycol, vegetable oils, and injectable organic esters. Aqueous carriers that could be used in formulating said composition of the present invention may include water.

Said composition of the present invention may also be suitable for oral administration, which may be presented as capsules or tablets, each containing a predetermined amount of baicalein; as a powder or granules; as solution; or as an oil-in-water liquid emulsion.

A person skilled in the art can easily determine appropriate dose, schedule, and method of administration for the exact formulation of the composition being used, in order to achieve what is desired as the "effective amount" in an individual patient. Said dose may vary depending on the mode of administration, age, and body weight of a patient, the symptom developed by the patient and the like. The term "effective amount" herein can be defined as, for example as the blood or tissue level desired in the patient that corresponds to a concentration of baicalein of said composition of the present invention. The person skilled in the art can also be readily determine and use an appropriate indicator of the "effective amount" of said composition of the present invention by pharmacological end-point analysis.

Below is an example of different optimum concentration of baicalein in reducing the flavivirus, dengue virus and Japanese encephalitis virus replication and viral RNA replication, from which the advantages of the present invention may be more readily understood. It is to be understood that the following example is for illustrative purpose only and should not be construed to limit the present invention in any way.

EXAMPLE A

Example A shows a composition of baicalein that exhibits prophylactic effects on dengue virus type-2 (DENV-2).

In order to determine the prophylactic anti-dengue activity of baicalein, different concentrations of baicalein (6.25 µg/ml, 12.50 µg/ml, 25.0 µg/ml, and 50.0 µg/ml) were added to the Vero cell monolayers five hours before adding virus. After five hours of pre-infection treatment, the cells were washed twice with phosphate-buffered saline (PBS). Then, 200 FFU (focus-forming units) of dengue virus type-2 (DENV-2) was inoculated to the cells to produce infected cells. The infected cells were incubated at 37° C. for one hour. Then the infected cells were washed two times with PBS to eliminate the unadsorbed viruses. Growth medium (the growing medium is but not limited to Eagle's minimal essential medium; EMEM) was supplemented with 2% fetal bovine serum (FBS), 1 mM non-essential amino acid solution, 1 mM L-glutamine solution, and 1.5% carboxymethyl cellulose (CMC) solution was added to the infected cells in the microplate. The microplate was incubated at 37° C. for four days. The number of viral foci formed and the viral RNA level were determined. The prophylactic activity of baicalein against DENV-2 was measured by the decrease in the number of viral foci and reduction of viral RNA synthesis. The number of DENV-2 foci was counted using a stereomicroscope and the titer of virus was expressed as FFU. The percentage of foci reduction (RF %) compared against controls was calculated as follows: RF (%)=(C−T)×100/C, where, C is the mean of the number of foci for negative control (without baicalein) and T is the mean of the number of foci in treated wells. Reduction in the number of viral foci was further verified using quantitative RT-PCR (qRT-PCR) which determine the copy number of dengue virus specific RNA. The same procedure was repeated to Vero cells which were treated with only virus suspension without baicalein (non-treated cells) and this served as the untreated control.

FIGS. 1(a) and (b) showed that pre-treatment of Vero cells with 50 µg/ml of baicalein reduced the number of dengue virus foci formed by ~37% and reduced the level of dengue virus type-2 RNA production by 39.5%±0.8, respectively compared to non-treated cells. The $IC_{50}$ of baicalein in pre-treatment of cells was 108.8 µg/ml. $IC_{50}$ (half maximal inhibitory concentration) is a measure of the effectiveness of a compound (baicalein) in inhibiting biological or biochemical function (of cells infected with DENV-2).

EXAMPLE B

Example B shows a composition of baicalein that shows inhibition of DENV-2 attachment to host cells.

Inhibition of DENV-2 attachment to host cells was evaluated by adding different concentrations (3.12 µg/ml, 6.25 µg/ml, 12.5 µg/ml, 25.0 µg/ml, and 50.0 µg/ml) of baicalein to Vero cells simultaneously with 200 FFU DENV-2. Then, the infected Vero cells were incubated at 37° C. for one hour in the presence of the respective concentration of baicalein. Following after, the infected Vero cells were washed two times using sterile PBS. Growth medium supplemented with 2% fetal bovine serum (FBS), 1 mM non-essential amino acid solution, 1 mM L-glutamine solution, and 1.5% carboxymethyl cellulose (CMC) solution) was added to the infected cells in the microplate. The microplate was incubated at 37° C. for four days. The number of viral foci formed and the viral RNA level were determined. The amount of viral RNA synthesis was determined using quantitative real time polymerase chain reaction amplification (qRT-PCR).

Figure 2A:
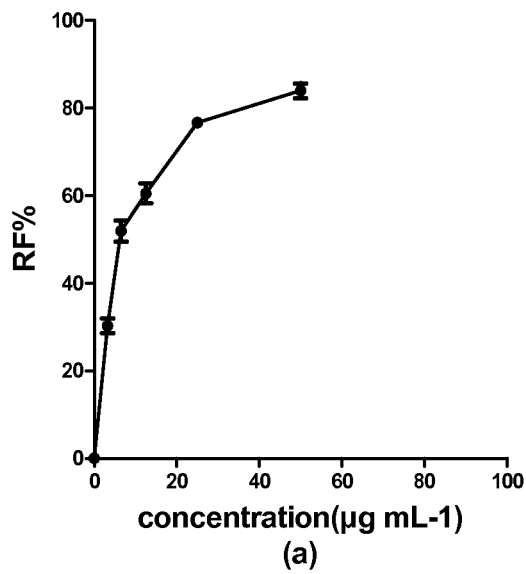
Figure 2B:
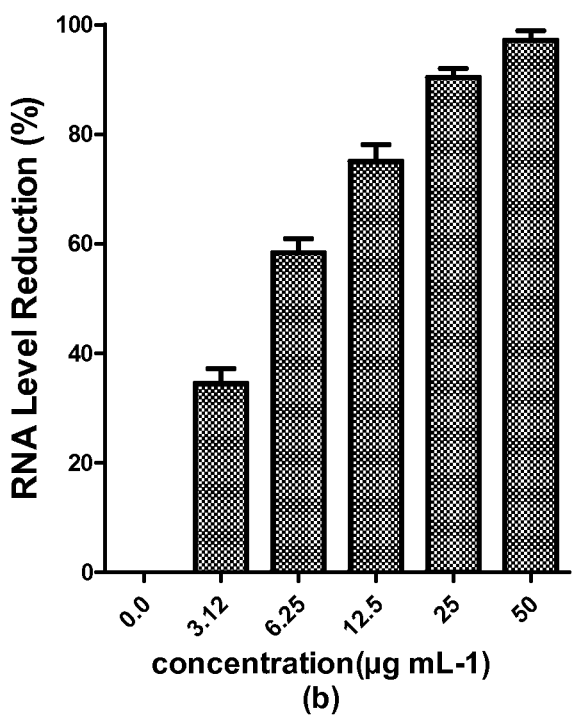

Results are shown if FIG. 2. FIGS. 2(a) and (b) showed that 25 µg/ml of baicalein reduced the number of dengue virus foci formed by 76.6% and decreased the level of DENV-2 RNA production by 90.3%±1.6 compared to the non-treated cells and the $IC_{50}$ value was calculated to be at 7.14 µg/ml (Higher decrease in RNA level was observed for 50 µg/ml)

EXAMPLE C

Example C shows a composition of baicalein that shows antiviral activity on dengue virus type-2 (DENV-2) replication when added post-infection.

In order to evaluate the antiviral activity of baicalein after virus attachment to cells, virus inoculum consisting of 200 FFU DENV-2 was added to the monolayer Vero cells and the virus was allowed to adsorp to the Vero cells for one hour at a temperature of 37° C. Unadsorped viruses were removed by rinsing the Vero cells with sterile PBS for two times. Different concentrations of baicalein (3.12 µg/ml, 6.25 µg/ml, 12.5 µg/ml, 25.0 µg/ml, and 50.0 µg/ml) were mixed with 1.5% CMC containing cell-growth medium supplemented with 2% FBS respectively before incubated at 37° C. for four days. Then, the number of viral foci and viral RNA level were measured.

Figure 3:
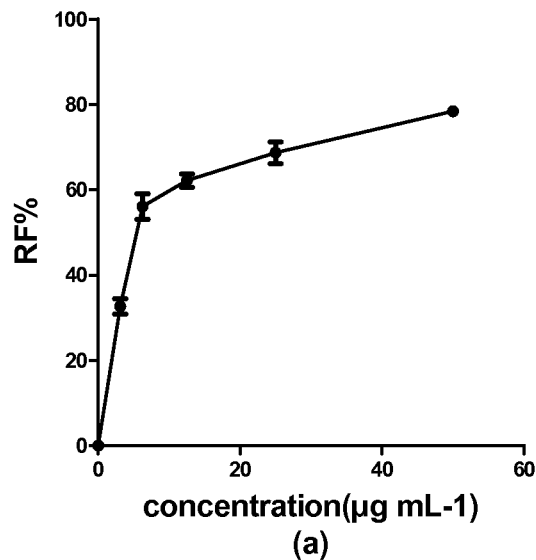
Figure 3B:
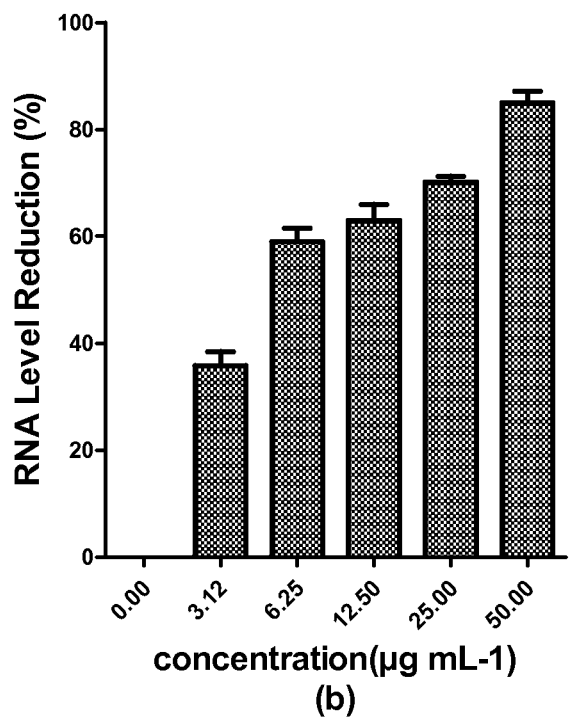

FIGS. 3(a) and (b) showed that 50 µg/ml of baicalein reduced the number of dengue virus foci formed by 78.3% and decreased the level of DENV-2 RNA production by 84.9%±2.15 compared to the non-treated cells and the $IC_{50}$ value was at 6.46 µg/ml.

EXAMPLE D

Example D shows a composition of baicalein that shows direct virucidal activity on dengue virus type-2 (DENV-2).

In order to determine the direct virucidal activity of baicalein against DENV-2, DENV-2 suspension containing 200 FFU was incubated with different concentrations of baicalein (1.56 µg/ml, 3.12 µg/ml, 6.25 µg/ml, 12.50 µg/ml, 25.0 µg/ml) at 37° C. for two hours to produce a treated viral suspension. Then, Vero cells were mixed with the treated viral suspension to produce infected cells. After one hour adsorption at 37° C., the infected cells were washed twice with PBS to remove unadsorped viruses. Growth medium supplemented with 2% fetal bovine serum (FBS), 1 mM non-essential amino acid solution, 1 mM L-glutamine solution, and 1.5% carboxymethyl cellulose (CMC) solution) was added to the infected cells in the microplate. The microplate was incubated at 37° C. for four days. The number of viral foci formed and the viral RNA level were determined.

Figure 4A:
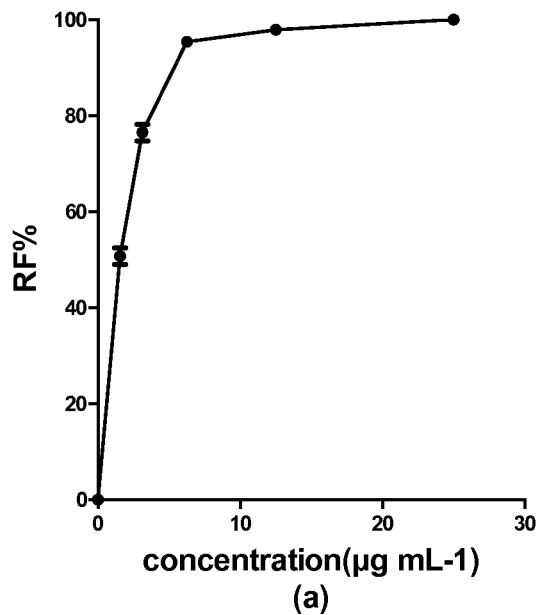
Figure 4:
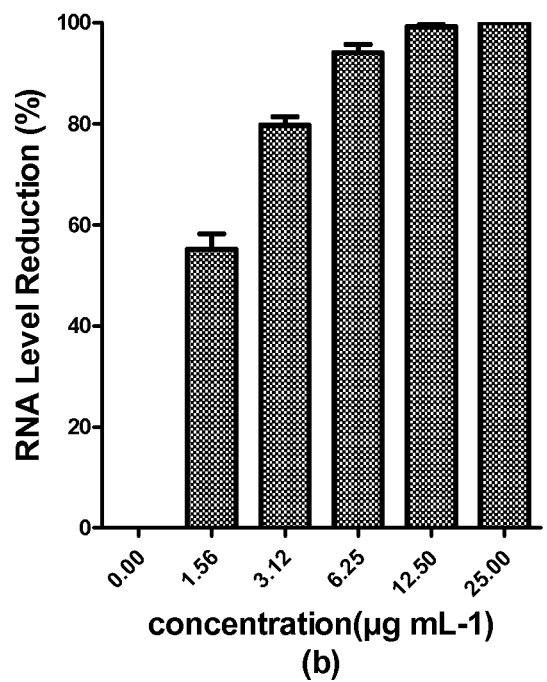

FIGS. 4(a) and (b) showed that 12.5 µg/ml of baicalein reduced the number of dengue virus foci formed by 97.93% and decreased the level of DENV-2 RNA production by 99.2%±0.4 compared to non-treated cells and its IC50 value was 1.55 µg/ml.

EXAMPLE E

Example E shows a composition of baicalein that shows antiviral activity on Japanese encephalitis (JE) replication when added post-infection.

In order to evaluate the antiviral activity of baicalein after virus attachment to cells, virus inoculum consisting of 200 FFU JE was added to the monolayer Vero cells and the virus was allowed to adsorp to the Vero cells for one hour at a temperature of 37° C. Unadsorped viruses were removed by rinsing the Vero cells with sterile PBS for two times. Different concentrations of baicalein (12.5 µg/ml, 25.0 µg/ml, 50.0 µg/ml and 100.0 µg/ml) were mixed with 1.5% CMC containing cell-growth medium supplemented with 2% FBS respectively before incubated at 37° C. for two days. Then, the number of viral foci was determined.

Figure 5:
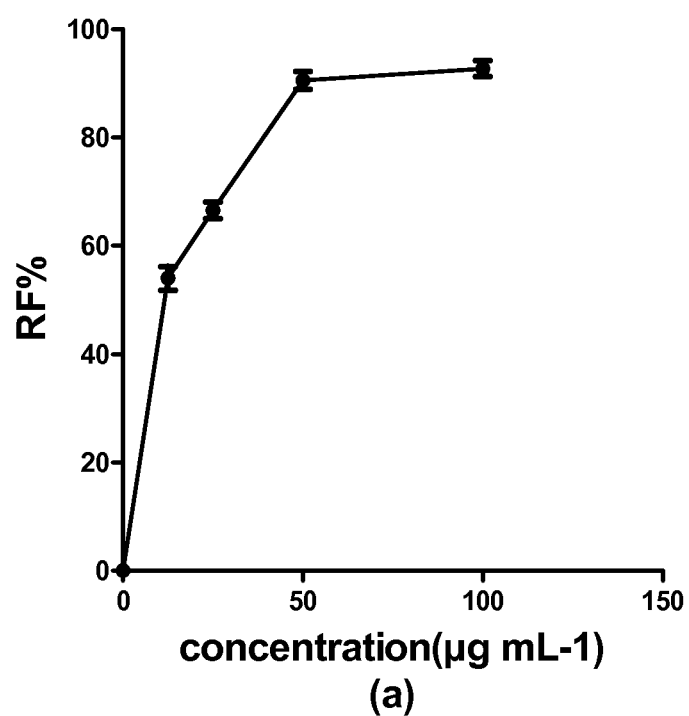

FIG. 5 showed that 50 µg/ml of baicalein added post-infection reduced the number of Japanese encephalitis virus foci formed by >90% compared to non-treated cells.

Although the present invention has been described with reference to specific embodiments, also shown in the appended figures, it will be apparent for those skilled in the art that many variations and modifications can be done within the scope of the invention as described in the specification and defined in the following claims.

I claim:

1. A method of treating an infection by a Flavivirus in a subject in need thereof which comprises administering to the subject an effective amount of baicalein which has the following structure and wherein the Flavivirus is dengue virus type-1, dengue virus type-2, dengue virus type-3, dengue virus type-4, or Japanese encephalitis virus.

2. The method according to claim 1, wherein the baicalein is administered to the subject in the form of a composition having the baicalein in a concentration ranging from 0.1 to 100% by weight.

3. The method according to claim 1, wherein the baicalein is administered to the subject in the form of a composition having the baicalein in a concentration ranging from 1.6 µg/ml to 100.0 µg/ml.

4. The method according to claim 2, wherein the composition is extracted from a plant.

5. The method according to claim 3, wherein the composition is extracted from a plant.

6. The method according to claim 2, wherein the composition is formulated with a pharmaceutically acceptable carrier.

7. The method according to claim 3, wherein the composition is formulated with a pharmaceutically acceptable carrier.

8. The method according to claim 1, wherein the baicalein is administered to the subject in the form of a composition comprising 50 µg/ml of the baicalein.

9. The method according to claim 1, wherein the baicalein is administered to the subject in the form of a composition comprising 25 µg/ml of the baicalein.

10. The method according to claim 1, wherein the baicalein is administered to the subject in the form of a composition comprising 12.5 µg/ml of the baicalein.

* * * * *